United States Patent [19]

Cohen et al.

[11] Patent Number: 5,318,858

[45] Date of Patent: Jun. 7, 1994

[54] ANTACID COMPOSITION

[76] Inventors: Gilbert Cohen, 37, Avenue Charles Floquet, Paris, France, 75007; Jacques Guillet, 39, Avenue Michelet, Agen, France, 47000

[21] Appl. No.: 933,216

[22] Filed: Aug. 20, 1992

Related U.S. Application Data

[63] Continuation-in-part of Ser. No. 835,500, Feb. 14, 1992, abandoned.

[51] Int. Cl.$^5$ .................. A61K 33/08; A61K 33/42
[52] U.S. Cl. ..................... 424/601; 424/692; 424/682
[58] Field of Search ............ 424/601, 682, 692

[56] References Cited

PUBLICATIONS

Remington's Pharmaceutical Sciences, 15th ed., 1975, Easton, Pa., Mack Publishing Co. pp. 731-735 and 1595-1596.

Carson et al., "Chemistry of the antacids: its relevance to antacid therapy", published in F. Halter ed. Antacids in the Eighties 1982, pp. 7-16.

J. Vatier et al., Aliment. Pharmacol. Therap. (1988), 2, pp. 461–470.

G. Martin, Jrnl. of Chem. Educ., (1988), 65 (No. 3), pp. 214–215.

*Primary Examiner*—Jerome D. Goldberg
*Assistant Examiner*—Phyllis G. Spivack
*Attorney, Agent, or Firm*—Jacobson, Price, Holman & Stern

[57] ABSTRACT

This invention is concerned with a novel antacid composition, said composition comprising, in association with a physiologically acceptable excipient, a pharmaceutically effective amount of a mixture of (a) an Al-containing material which normally adheres to the gastrointestinal mucous membrane, as a first pharmaceutically active component, and (b) a Mg-containing material which normally does not adhere to the gastrointestinal mucous membrane, as a second pharmaceutically active component, wherein the weight ratio of Al in said Al-containing material to Mg in said Mg-containing material is 5.1:1 to 7.0:1.

Said composition is particularly useful in the treatment of dyspepsia.

11 Claims, No Drawings

ANTACID COMPOSITION

CROSS REFERENCE

This invention is a continuation-in-part of a previous U.S. patent application, Ser. No. 07/835,500 filed on Feb. 14, 1992 now abandoned. It comprises elements regarding the compositions of Examples 1-4 disclosed in said previous application and new data concerning the weight ratio Al/Mg.

FIELD OF THE INVENTION

This invention is concerned with a novel antacid composition which is useful in the treatment of dyspepsia. Said antacid composition comprises an Al-containing material (preferably an $AlPO_4$-containing material), as a first pharmaceutically active component, and a Mg-containing material, which is preferably selected from the group consisting of MgO and $Mg(OH)_2$, as a second pharmaceutically active component.

PRIOR ART

In a general manner, (i) Al-containing materials such as aluminum hydroxide and aluminum salts, in particular the aluminum phosphate and aluminum carbonate salts, are normally adhering (in the gel form) to the gastrointestinal mucous membrane, but are not normally effective as antacid products; and (ii) Mg-containing materials, such as MgO and $Mg(OH)_2$, are known to be effective as antacid products, but do not normally adhere to the gastrointestinal mucous membrane.

Attempts to combine into a single antacid composition an Al-containing component and a Mg-containing component are mentioned on page 14 (paragraph "Current Antacid Formulations") of the paper by G. L. CARLSON and J. R. MALAGELADA entitled: "Chemistry of the antacids: its relevance to antacid therapy" published in F. HALTER ed. "*Antacids in the Eighties*", URBAN & SCHWARZENBERG, Munich, 1982, pages 7–16.

To be precise those attempts were concerned with compositions containing aluminum hydroxide and magnesium hydroxide as recited in said G. L. CARLSON and J. R. MALAGELADA paper. The corresponding antacid compositions, which were commercially successful in the USA, in particular in the "over-the-counter" (OTC) market, comprise the following US specialties, namely:

(A) MAALOX-TC TM, a suspension commercialized by the US firm RHONE-POULENC RORER, Philadelphia, which contains per teaspoon 600 mg of aluminum hydroxide and 400 mg of magnesium hydroxide;

(B) MYLANTA II TM, a suspension commercialized by the US firm STUART PHARMACEUTICALS, Wilmington, Del., which contains per teaspoon 400 mg of aluminum hydroxide and 400 mg of magnesium hydroxide; and (C) RIOPAN TM, a suspension commercialized by the US firm WHITEHALL LABS, New York, N.Y., which contains per teaspoon 540 mg of "magaldrate", an aluminum magnesium hydroxide $(AlMg(OH)_7)$ monohydrate compound which is disclosed in particular in the Merck Index 11th edition, page 890, monograph number: 5527, (1989).

These three (A)–(C) US market-leading liquid antacid specialties exhibit an in vitro antacid activity having a rather short duration (about 2-3 hours) according to the experimental technique disclosed by J. VATIER et al., in *Aliment. Pharmacol. Therap.*, (1988), 2, 461–470 (incorporated herein as reference) and an in vitro antacid isolating capacity (as explained hereinafter) having a too short duration (at most 3.5 minutes, especially for specialty (C), i.e. RIOPAN TM, for decreasing back to a pH of 2.0).

In these three (A)–(C) antacid specialties, the weight ratio (R) of Al present in the Al-containing material to Mg present in the Mg-containing material varies from about 0.8 to about 1.3, namely R is 1.24 for specialty (A), i.e. MAALOX-TC TM, 0.83 for specialty (B), i.e. MYLANTA II TM, and 1.10 for specialty (C), i.e. RIOPAN TM. In a general manner, the antacid specialties, which were provided up to now, have a ratio R lower than or equal to 2.5:1 and do not exhibit any anti-ulceration property nor any Al-adhesiveness on the gastric mucous membrane.

On the other hand, there is an Al-containing compound, namely sucralfate, which has been successfully commercialized in the USA as an anti-ulcer product. The sucralfate compound, which is in particular disclosed in the Merck Index, 11th edition, page 1400, monograph number 8853, (1989), is devoid of any antacid properties since it does meet the requirements of 21 C.F.R. 331. Its molecular formula is $C_{12}H_{54}Al_{16}O_{75}S_8$ and its structure is

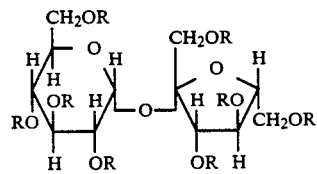

wherein R is $SO_3[Al_2(OH)_5]$.

In view of said formula and structure, the sucralfate compound is Mg-free. The sucralfate compound, after oral administration, provides an Al-adhesiveness duration of about 24 h on the ulcerated sites of the gastric mucous membrane, and of about 3-4 h when there is no ulceration.

AIM OF THE INVENTION

There is a need to look for a new antacid composition having a longer duration in both the J. VATIER et al. experimental technique and the antacid isolating capacity test than the previously known above cited antacid compositions.

OBJECT OF THE INVENTION

Said need is successfully met according to this invention. The new technical solutions which is provided involves the use of a mixture of an Al-containing material and a Mg-containing material wherein the weight ratio R is equal to or a higher than 5.1:1, in order to obtain both the Al-adhesiveness and the antacid activities.

According to a first aspect of this invention, a novel antacid composition is provided which comprises, in association with a physiologically acceptable excipient, an effective amount of a pharmaceutically antacid mixture of (a) an Al-containing material which normally adheres to the gastrointestinal mucous membrane, as a first pharmaceutically active component, and (b) a Mg-containing material which normally does not adhere to said gastrointestinal mucous membrane, as a second pharmaceutically active component, wherein the weight ratio of Al in said Al-containing material to Mg in said Mg-containing material is equal to or higher than 5.1:1, said Al-containing material/Mg-containing material mixture satisfying the antacid requirements of 21 C.F.R. 331 and providing an Al-adhesiveness duration on the gastrointestinal mucous membrane which is at least as long as the one of the sucralfate compound.

On the first hand, said antacid composition fully meets the requirements of 21 C.F.R. 331 (which are reported hereinafter), gives an in vitro antacid activity higher than or equal to 5 h according to the J. VATIER et al. experimental technique, and an in vitro antacid isolating capacity higher than or equal to 9 minutes for decreasing back to a pH of 2.0.

On the other hand, said composition is effective to provide an Al-adhesiveness with a long duration over the gastrointestinal mucous membrane. It exhibits a long-lasting coating action which is specific for the ulcerations of the gastrointestinal mucous membrane, since its Al-containing component (or the Al issuing therefrom) remains coated over the ulcerative sites of the gastrointestinal mucous membrane for at least 24 hours after oral administration providing therefore a protection of those ulceration sites, whereas said Al-containing component remains coated over the non-ulceration portions of said gastrointestinal mucous membrane for 4–6 hours after oral administration.

In short, the composition according to this invention does exhibit the double advantage to be (i) effective as antacid, which is not the case of the sucralfate compound, and (ii) effective to provide a long Al-adhesiveness duration on the gastrointestinal mucous membrane like the sucralfate compound. To be more precise, the composition according to this invention is at least as active as said sucralfate compound, where the Al-adhesiveness duration (or the anti-ulceration property) is concerned.

The composition according to this invention provides a specific long-lasting Al-adhesiveness duration on the gastrointestinal mucous membrane equal to or higher than 24 h on the ulceration sites of said gastrointestinal mucous membrane. Such an Al-adhesiveness duration gives a specific long-lasting anti-ulceration coating protection over the ulceration sites of the gastrointestinal mucous membrane.

According to a second aspect, a method of treatment of dyspepsia is provided which comprises administering to a human being in need of such a treatment a therapeutically effective amount of the antacid composition according to this invention. Dyspepsia means here any digestion trouble, and the composition according to this invention is particularly destined to digestion troubles induced by gastric hyperacidity.

DETAILED DISCLOSURE OF THE INVENTION

The term "ulceration" means here any alteration of the gastrointestinal mucous membrane and generically includes both (i) an ulcer alteration, and (ii) a non-ulcer (or ulcer-like) alteration of said gastrointestinal mucous membrane.

The expression "ulceration sites" designates sites having either an ulcer alteration or a non-ulcer alteration, whereas the expressions "ulcerative sites" and "ulcerated sites" designated sites having only an ulcer alteration.

The first pharmaceutically active component according to the invention is an Al-containing material, which normally adheres to the gastrointestinal mucous membrane. Such a material includes in particular any compounds freeing $Al^{3+}$ in the gastrointestinal tract, especially in the gastric juice, such as $Al(OH)_3$ and aluminum salts. Among the aluminum salts, which can be used in this invention, can be cited in particular the aluminum phosphate, aluminum carbonate, aluminum magnesium silicate of the formula $MgAl(SiO_4)_2$, organic aluminum sulfonates and sulfates, such as the sucralfate compound, and mixtures thereof. Alternatively the Al-containing material can also contain Mg; in such a case that material is an Al and Mg source.

The preferred sources of Al according to this invention, which provide $Al^{3+}$ ions, are $AlPO_4$-containing materials and aluminum sulfate and/or sulfonate containing materials. By the expression "$AlPO_4$-containing material" is meant here a product which is $AlPO_4$ or contains $AlPO_4$. By the expression "aluminum sulfate and/or sulfonate containing material" is meant here a (preferably organic) aluminum sulfate or sulfonate compound. Among the products which contain $AlPO_4$ can be cited the aluminum phosphate gels, in particular those having an $AlPO_4$ content of from 5 to 45% by weight, and among the aluminum sulfate or sulfonate containing materials the sucralfate compound.

Such an $AlPO_4$-containing or aluminum sulfate/sulfonate containing material, when used in combination with the Mg-containing material according to this invention, normally adheres (i) to the gastric mucous membrane, when there is no ulceration, for about 4–6 h, and (ii) to the gastrointestinal mucous membrane at the gastric or respectively the duodenal mucous membrane, when there are gastric or respectively duodenal ulcerations, for at least 24 h. However, said Al-containing material is considered as being normally non-antacid by the FDA since it does not generally meet the requirements of 21 C.F.R. 331.

The preferred compound useful as an Al-containing material is here an $AlPO_4$-containing material, namely an aluminum phosphate gel, and more preferably an aluminum phosphate gel containing 20% by weight of $AlPO_4$.

The second pharmaceutically active component according to the invention, i.e. the Mg-containing material, is preferably selected from the group consisting of $MgO$, $Mg(OH)_2$ and mixtures thereof. The most preferred Mg-containing material is here $MgO$.

$MgO$ and $Mg(OH)_2$ are in a general manner normally non-adhering to the gastrointestinal mucous membrane, and are considered as normally effective as antacid products since they generally do meet the requirements of 21 C.F.R. 331. However, they are not sufficient per se when used alone without any Al-containing material to provide a long-lasting protection on the gastrointestinal mucous membrane, and therefore a protective anti-ulceration coating over the ulceration sites.

According to this invention, it has been found that the Al-adhesiveness on the gastrointestinal mucous membrane, in particular on the gastric mucous membrane, induces an increase in the antacid effect duration of the Mg-containing material.

It is critical according to this invention that the weight ratio (R) of the total amount of Al in said Al-containing material to the total amount of Mg in said Mg-containing material is equal to or higher than 5.1:1.

When R is equal to or higher than 5.1:1 there is a synergetic increase in both the Al-adhesiveness and the antacid duration. To be precise the Al-adhesiveness on the gastrointestinal mucous membrane prolongs surprisingly the antacid effect duration.

When R is lower than 5.1×1 there is a decrease in both the adhering capacity (mainly) and the antacid activity of the resulting composition of said Al-containing material with said Mg-containing material. The upper limit value of R is a function of the antacid requirement of 21 C.F.R. 331. Indeed when the ratio R increases and reaches a value for greater than 5.1:1, the resulting composition becomes non antacid. For instance, when the Mg-containing material is not present (as it is the case in the sucralfate compound), the resulting product is no longer effective as an antacid material. In short, when the ratio R is higher than 7.0:1, the resulting Al-containing material/Mg-containing material composition is considered as non effective as an antacid product in view of the 21 C.F.R. 331 requirements. According to this invention, it is recommended that the ratio R is comprised between 5.1:1 and 7.0:1, preferably between 5.5:1 and 6.5:1 and more preferably between 5.9:1 and 6.1:1.

BEST MODE OF THE INVENTION

The composition according to the invention, which comprises said Al-containing material and said Mg-containing material with a weight ratio R equal to or higher than 5.1:1 and more preferably a weight ratio R of from 5.1:1 to 7.0:1, is useful in the treatment of dyspersia. Said composition is particularly useful in the treatment of digestion troubles induced by gastric hyperacidity.

The best mode according to the invention consists in (i) providing an antacid composition containing per unit dose 9.904 g of an aluminum phosphate gel containing 20% by weight of AlPO$_4$ (i.e. a total amount of 1.98 g of AlPO$_4$) and 0.122 g of MgO, and having a weight ratio R of about 6:1 (to be precise, R is in this case 5.95:1); and (ii) administering such a unit dose three times a day.

Such a unit dose is disclosed in example 1 hereinafter.

EXAMPLES AND ASSAYS OF THE INVENTION

Further advantages and characteristics of the invention will be understood more clearly from the following description of examples, assays and results of comparative tests. These data as a whole do not in any way imply a limitation but are given by way of illustration.

EXAMPLE 1

An antacid composition, according to the best mode of this invention, has been prepared in the form of a sachet containing the two active ingredients, the excipient and water, with the following formulation:

| | |
|---|---|
| 1) active ingredients | |
| aluminum phosphate gel (containing 20% by weight of AlPO$_4$; equivalent amount of AlPO$_4$: 1.98 g) | 9.904 g |
| magnesium oxide | 0.122 g |
| 2) excipient | |
| potassium sorbate | 0.042 g |
| pectin | 0.080 g |
| gum xantham | 0.032 g |
| sorbitol | 3.024 g |
| orange flavoring | 0.006 g |
| 3) water | |
| balance up to | 16.000 g |

The antacid composition of example 1, which has a weight ratio R=5.95:1, was conditioned in an aluminum foil sachet. The recommended daily dosage is 3 sachets.

21 C.F.R. 331 REQUIREMENTS

Antacid products for OTC or ethical human uses must meet the conditions which are specified in 21 C.F.R. 331; namely:

the active ingredients of the antacid composition consist of one or more of the ingredients permitted in paragraph 331.11 within any maximum daily dosage limit established;

each active ingredient must provide at least 25% of the total acid neutralizing capacity (ANC) of the antacid composition;

the finished antacid composition must contain at least 5 mEq of ANC;

the pH at the end of the initial period of 10 minutes in the preliminary antacid test must be 3.5 or greater.

The preliminary antacid test and the ANC test were carried out with the antacid composition of example 1 according to the technique described in 21 C.F.R. 331 (also found in the U.S. Pharmacopoeia XXII, pages 1624–1625).

A. Preliminary Antacid Test

Reagent standardization: sodium hydroxide (NaOH) and hydrochloric acid (HCl) solutions were standardized according to the procedures described in the U.S. Pharmacopoeia XVIII (on page 1036 for NaOH, and on page 1034 for HCl).

Temperature: all the test were conducted at 25°±2° C.

pH meter: the pH meter was standardized at pH 4.0 with a standardizing buffer and checked for proper operations at pH 1.0 with 0.1N HCl.

Test suspension: exactly 16.0 g of the well-mixed Ex 1 composition (i.e. 1 unit dose) were added into a 100 ml glass beaker and then 40 ml of distilled water were added; the resulting suspension was then mixed by means of a magnetic stirrer at 300±30 rpm for one minute.

Test procedure: 10.0 ml of 0.5N HCl were added to the test suspension while stirring at 300±30 rpm was continued for exactly 10 minutes; the pH was then recorded; the test was carried out in triplicate on two batches of Ex 1.

Result: the following result was obtained for Ex 1: pH=3.79.

Acid Neutralizing Capacity

Reagent standardization: as disclosed above.
Temperature: as disclosed above.
pH meter: as disclosed above.

Test suspension: the composition of Ex 1 was well-mixed and exactly 16.0 g (one unit dose) were transferred into a 250 ml glass beaker; sufficient water was added to obtain a total volume of about 70 ml; the resulting suspension was then mixed by means of a magnetic stirrer at 300±30 rpm for one minute.

Test procedure: 30.0 ml of 1.0N HCl were pipetted into the test suspension while stirring by means of the magnetic stirrer at 300±30 rpm; the suspension was then stirred for exactly 15 minutes after the addition of the acid; titration then began immediately; the excess of 1.0N HCl was titrated with 0.5N NaOH to a stable pH of 3.5 in a period of time not exceeding an additional term of 5 min; the test suspension was checked 10 to 15 s after obtaining pH 3.5 to be sure that the pH is stable.

Calculation of the mEq value: the number of mEq of acid neutralized by the test suspension was calculated as follows:

$$\text{total mEq} = (30.0) \times (\text{HCl normality}) - (\text{NaOH ml}) \times (\text{NaOH normality})$$

Result: for Ex 1, an ANC value of 12.12 mEq was obtained.

C. Contribution of Each Active Ingredient

Active ingredients: the following active ingredients were used, namely MgO and an aluminum phosphate gel containing 20% by weight of $AlPO_4$.

Reagent standardization: as disclosed above.
Temperature: as disclosed above.
pH meter: as disclosed above.
Test solution:
for aluminum phosphate
an accurately measured volume of an aluminum phosphate suspension containing exactly 9.904 g of aluminum phosphate gel, corresponding to the amount present in a one unit dose (16 g) of the antacid composition of Ex 1, were placed into a 250 ml glass beaker; distilled water was added up to a volume of 70 ml and the resulting suspension was mixed by means of a magnetic stirrer at 300±30 rpm for one minute;

for magnesium oxide
0.122 g of MgO, corresponding to the amount present in the one unit dose (16 g) of the antacid composition of Ex 1, was placed into a 250 ml glass beaker; distilled water was added up to a volume of 70 ml and the resulting aqueous medium was mixed by means of a magnetic stirrer at 300±30 rpm for one minute.

Test procedure: as disclosed above for the ANC test.
Calculation: the percent contribution of each active ingredient in the total antacid composition of Ex 1 was calculated as follows:

$$\% \text{ contribution} = \frac{(\text{total mEq antacid ingredient}) \times 100}{(\text{total mEq antacid composition})}$$

Results: the following results were obtained:
$AlPO_4$ contribution = 6.75 mEq (i.e. 56%)
MgO contribution = 4.88 mEq (i.e. 40%)

D. Conclusions

The maximum daily dosage of the antacid composition of Ex 1 (3 sachets a day) comprises 5.94 g of aluminum phosphate, that is to say a value which is lower than the maximum daily upper limit (8 g) as specified in 21 C.F.R. 331.

Consequently, the antacid composition of Ex 1 fully meets the requirements of 21 C.F.R. 331.

Moreover the results of the assays carried out with the composition of example 1 do point out that the association of the Al-containing material with the Mg-containing material according to this invention potentiates the antacid activity of the Al-containing material since said Al-containing material when used alone does not exhibit any antacid activity.

EXAMPLES 2–4

The following formulations were obtained by varying the weight ratio R.

| Ex 2 (R = 6.23:1) | |
|---|---|
| active ingredients | |
| aluminum phosphate gel (containing 20% by weight of $AlPO_4$; equivalent amount of $AlPO_4$: 1.70 g) | 8.503 g |
| magnesium oxide | 0.100 g |
| 2) excipient | |
| as in example 1. | |
| 3) water | |
| balance up to | 14.500 g |
| Ex 3 (R = 5.13:1) | |
| 1) active ingredients | |
| aluminum phosphate gel (containing 20% by weight of $AlPO_4$; equivalent amount of $AlPO_4$: 2.20 g) | 11.004 g |
| magnesium oxide | 0.157 g |
| 2) excipient | |
| as in example 1. | |
| 3) water | |
| balance up to | 17.000 g |
| Ex 4 (R = 6.33:1) | |
| 1) active ingredients | |
| aluminum phosphate gel (containing 20% by weight of $AlPO_4$; equivalent amount of $AlPO_4$: 2.02 g) | 10.104 g |
| magnesium hydroxide (corresponding to 0.117 g of MgO) | 0.170 g |
| 2) excipient | |
| as in example 1. | |
| 3) water | |
| balance up to | 16.300 g |

Examples 2–4 fully meet the requirement of 21 C.F.R. 331.

COMPARATIVE EXAMPLES CP 1–CP 4

The following Comparative formulations were obtained by varying the weight ratio R. comparative examples CP1 (R=5.07:1) and CP2 (R=7.04:1) were compounded in order to confirm the lower (R=5.1:1) and upper (R=7.0:1) limits of the weight ratio R according to this invention.

| CP 1 (R = 5.07 × 1) | |
|---|---|
| 1) active ingredients | |
| aluminum phosphate gel (containing 20% by weight of $AlPO_4$; equivalent amount of $AlPO_4$: 1.69 g) | 8.453 g |
| magnesium oxide | 0.122 g |
| 2) excipient | |
| as in example 1. | |
| 3) water | |
| balance up to | 14.500 g |
| CP 2 (R = 7.04 × 1) | |
| 1) active ingredients | |
| aluminum phosphate gel (containing 20% by weight of $AlPO_4$; equivalent amount of $AlPO_4$: 2.21 g) | 11.054 g |
| magnesium oxide | 0.115 g |
| 2) excipient | |
| as in example 1. | |
| 3) water | |
| balance up to | 17.000 g |
| CP 3 (R = 8.06 × 1) | |
| 1) active ingredients | |
| aluminum phosphate gel (containing 20% by weight of $AlPO_4$; equivalent amount of $AlPO_4$: 1.98 g) | 9.904 g |
| magnesium oxide | 0.090 g |

-continued 2) excipient
   as in example 1.
3) water
   balance up to                                    16.000 g

CP 4 (R = 4.77 × 1)

1) active ingredients
   aluminum phosphate gel (containing 20% by      9.904 g
   weight of AlPO$_4$; equivalent amount of
   AlPO$_4$: 1.98 g)
   magnesium oxide                                 0.152 g
2) excipient
   as in example 1.
3) water
   balance up to                                    16.000 g

ANTACID ACTIVITY in vitro—COMPARATIVE ASSAYS I

A. Preliminary Remarks

The acid neutralizing capacity (ANC), as recommended by the FDA, which is determined according to FORDTRAN et al., *N. Eng. J. Med.* (1973), 288, pages 923–928, is not a relevant measure of an antacid product's real or effective capacity. First of all, all antacid products neutralize nearly all the HCl present in the stomach when a recommended dose is ingested. Secondly, the usual in vitro measurements of antacid activity are insufficient, since they do not take into account the complexity of the gastric physiology. Finally, and most important, the ANC ignores the duration of antacid activity, which is more important than the ANC itself, see in particular the article of G. MARTIN, *Journal of Chemical Education* (1988), 65 (No. 3), pages 214–215.

For that reason, such an in vitro model possessing features of a normally functioning stomach was used to compare the efficiency of antacid products. With this model, Ex 1 and other antacid products were evaluated under conditions that mimic the therapeutic challenge faced in actual use. In particular, the antacid activity duration, which is the most pharmacologically relevant characteristic of an antacid product, was measured.

B. Procedure

The experimental model disclosed by J. VATIER et al., *Aliment. Pharmacol. Therap.*, (1988), 2, pages 461–470 (see schematic representation appearing in FIG. 1 on page 462) was used. It comprised a "gastric" reservoir, in which the entering and emptying fluxes occurred, a peristaltic pump producing both fluxes, and a pH measuring and recording system.

In the first experiment, the reservoir was filled with 100 ml of 0.1N HCl. In the second experiment, 100 ml of 0.1N HCl were added into the reservoir on the wall of which a 3×20 cm segment of fresh gastric mucous membrane had been fixed. The experiments were started (T=0) by the addition of the antacid product to be tested in the "gastric" reservoir. Continuous mixing was obtained with a magnetic stirrer. After the reservoir had been filled with the product to be tested, the peristaltic pump was started. The pH of the contents was monitored continuously throughout the experiment until it returned to the initial value. For each product to be tested three assays were carried out. The results, as given hereinafter are expressed as the mean of these assays. The interassay variation was lower than 4%.

The pH curves as recorded were analyzed to obtain the following values:
time (in minutes) during which the pH remained above the initial value,
mmol H$^+$ neutralized before the pH returned to its initial value.

C. Materials

Comparative assays were carried out with (i) examples 1–4 according to this invention, (ii) comparative formulations CP 1–CP 4, and (iii) previously known antacid specialties A–C as cited above and used according to their recommended respective dosages.

D. Results

The results thus obtained are tabulated in tables Ia, Ib and Ic hereinafter. They clearly point out that the antacid compositions of examples 1–4 according to the invention exhibit a higher antacid activity than comparative compositions CP 1–CP 4 and specialties A–C.

Moreover, the results of said tables Ia, Ib and Ic show that the ANC value is not a pharmacologically relevant measure, since for instance the ANC values of Ex 1, A, B and respectively C, which are 9.6, 27.2, 25.4 and respectively 15.0 mEq, do not reflect the real or effective antacid activity as measured with the experimental model of J. VATIER et al. cited above.

ANTACID ISOLATING CAPACITY—COMPARATIVE ASSAYS II

The antacid isolating capacity is modelled in a simple in vitro experiment, in which a pH electrode is first coated with a suspension of an antacid composition to be tested, then dipped into a HCl bath. The pH, which is recorded over the 15 minute period which follows, indicates how the antacid composition to be tested adheres to said electrode and isolates its pH-sensitive tip (simulating the gastric mucous membrane) from the H$^+$ in the surrounding bath.

A. Materials And Method

The antacid compositions to be tested were (i) the antacid compositions of examples 1–4 according to the invention, (ii) the comparative formulations of CP1–CP4, (iii) previously known antacid specialties A–C, and (iv) other antacid specialties of the US market namely:

(D) ALUDROX ™, a suspension commercialized by the U.S. firm WYETH-AYERST LABS, Radnor, Pa., which contains per teaspoon 307 mg of aluminum hydroxide and 103 mg of magnesium hydroxide (R=1.89:1); and, (E) DIGEL ™ sodium free, a suspension commercialized by the U.S. firm PLOUGH INC., Memphis, Tenn., which contains per teaspoon 200 mg of aluminum hydroxide and 200 mg of magnesium hydroxide (R=1.61:1).

Reagent standardization: sodium hydroxide (NaOH) and hydrochloric acid (HCl) solutions were standardized according to the procedures described in the U.S. Pharmacopoeia XVIII (NaOH page 1036, HCl page 1034).

Temperature: all the test were conducted at 25° C.±3° C.

pH meter: the pH meter was standardized at pH 4.0 with a standardizing buffer and checked for proper operations at pH 1 with 0.1N HCl.

Test procedure: 50 g of an antacid product to be tested are introduced into a pre-weighed glass cylinder having a diameter of 3 cm and a volume capacity of 80 ml; a pH electrode is carefully introduced into the antacid-containing cylinder where it remains for 40 seconds; the electrode is then carefully withdrawn from the antacid-containing cylinder and the antacid product is allowed to drain along the electrode for the next 40 seconds; the introducing/withdrawing operation is repeated 5 times; the antacid-containing cylinder is weighed accurately in order to determine the amount of antacid product remaining on the electrode; the electrode thus coated is carefully and vertically introduced into a glass beaker containing 100 ml of 0.1N HCl, the lower tip of the coated electrode being placed 2 cm above the bottom of the beaker; the pH is then read and recorded for 15 minutes.

B. Results

The results which were obtained are given in table II hereinafter. They clearly point out that the antacid compositions of examples 1–4, unlike the comparative compositions CP1–CP4 and the previously known specialties A–E, do exhibit a higher antacid isolating capacity (at least 12 minutes, and more than 12 minutes with example 1, for returning to a pH of 2.0).

Moreover the data of tables Ia, Ib, Ic and II do show the interest of the antacid compositions of examples 1–4 according to the invention, which comprise an Al-containing material (here an aluminum phosphate gel containing 20% by weight of aluminum phosphate), as a first pharmaceutically active component, and a Mg-containing material (here MgO or Mg(OH)$_2$), as a second pharmaceutically active component, wherein the weight ratio R of the total Al in said Al-containing material to Mg in said Mg-containing material is comprised between 5.1:1 and 7.0:1, from a pharmaceutically point of view with respect to both the antacid activity and the antacid isolating capacity.

SCINTIGRAPHIC IMAGING

It had been difficult up to now to demonstrate in vivo the protecting effect of an antacid product on the gastrointestinal mucous membrane, in particular at the level of the stomach and the duodenum. After testing several nuclide materials having suitable gamma energies in the range of from 60 to 500 keV, such as $^{99m}$technetium-containing materials ($^{99m}$Tc-sulfur colloids, $^{99m}$Tc-albumin microspheres, $^{99m}$Tc-dimercaptosuccinic acid complexes, $^{99m}$Tc-polyphosphates, -pyrophosphates and -diphosphonates), it appeared that $^{99m}$Tc-hydroxymethylene diphosphonate ($^{99m}$Tc-HMDP) is the most suitable radiopharmaceutical material for labelling aluminum phosphate gel-containing antacid material. Said $^{99m}$Tc-HMDP compound is the only one, amongst the tested radionuclide compounds, to exhibit a high labelling efficiency and to be substantially non-adsorbed onto the wall (mainly glass) of the reaction vessels or tubes.

A. Assays with AlPO$_4$ Gel Labelled with $^{99m}$Tc-HMDP

Assays with $^{99m}$Tc-HMDP-labelled AlPO$_4$ gel were carried out in acid solution and in gastric and duodenal juices in vitro.

In HCl:

Aluminum phosphate gel (22 g) was first labelled with $^{99m}$Tc-HMDP (37 MBq). Then 1.5 ml of the $^{99m}$Tc-HMDP-labelled AlPO$_4$ gel thus obtained was pipetted into each of 22 hemolysis tubes. 1.0 ml of HCl (20°-21° Bé) was added to 11 of the hemolysis tubes, 1.0 ml of HCl (10° Bé) was added to 7 of the hemolysis tubes, and 1.0 ml of saline solution containing 9 g/l of NaCl was added to the remaining 4 hemolysis tubes (as control tubes). After shaking said 22 hemolysis tubes for one hour, the $^{99m}$Tc-HMDP-labelled AlPO$_4$ gel became translucent. The hemolysis tubes were shaken for another hour, then centrifuged at 3500 rpm for 15 minutes. Counting and imaging of the hemolysis tubes and supernatants were carried out.

The results thus obtained, tabulated in table III hereinafter, (i) confirm the high quality of the labelling: 73–74% of the initial radioactivity remained bound to the aluminum phosphate gel in the presence of high HCl concentrations, and more than 90% of the initial radioactivity remained bound in the saline control tubes, and (ii) show that the stability of the $^{99m}$Tc-HMDP-labelled AlPO$_4$ gel is satisfactory, as pointed out in HCl concentrations exceeding those existing in the gastrointestinal tract.

In gastric or duodenal juices in vitro:

The above experiment was repeated with samples of human gastric and duodenal juices, obtained from voluntary subjects, in order to replace HCl. The results thus obtained are given in table IV hereinafter. They show that about 90% of the initial radioactivity remained bound after the hemolysis tubes containing 1.5 ml of $^{99m}$Tc-HMDP-labelled AlPO$_4$ gel plus 1.0 ml of either gastric (2 hemolysis tubes) or duodenal (3 hemolysis tubes) juices where shaken for 2 hours, and that the difference in pH between gastric juice (pH of about 2) and duodenal juice (pH of about 6.5) does not modify the bound remaining radioactivity.

Viscosity, adhesiveness and pH:

In the experiments described, (i) the viscosity and adhesiveness (to glass) of AlPO$_4$ gel and of $^{99m}$Tc-HMDP-labelled AlPO$_4$ gel were not different, (ii) the effect of the acid on AlPO$_4$ gel and on $^{99m}$Tc-HMDP-labelled AlPO$_4$ gel was the same, these two products becoming translucent at low pH. Therefore, labelling AlPO$_4$ gel with $^{99m}$Tc-HMDP does not altere the in vitro properties of the AlPO$_4$ gel, and the $^{99m}$Tc-HMDP-labelled AlPO$_4$ gel is stable in neutral, acid and alkaline conditions.

B. Clinical Assays

1) Patients:

A group of 24 patients, all voluntary, suffering from abdominal pain were subjected to an endoscopic examination (showing that 11 patients had a gastric ulcer, 3 patients had a duodenal ulcer, and the remaining 10 patients had abdominal pain without fibroscopic evidence of ulcer or other mucosal alteration disease) then administered with the antacid composition of example 1 according to this invention previously labelled with $^{99m}$Tc-HMDP.

2) Labelling:

22 g of the antacid composition of example 1 were labelled with 37 MBq of $^{99m}$Tc-HMDP in a plastic tube. The resulting radiopharmaceutical labelled product was allowed to rest for 5 minutes before ingestion per oral route.

3) Isotope scanning procedure:

Scanning was carried out within 72 h after endoscopy. After an overnight fast, each patient received per os (i) 20 ml of the labelled antacid composition of example 1 wherein the aluminum phosphate gel was labelled with said $^{99m}$Tc-HMDP, then (ii) 200 ml of water. Imaging was carried out with the supine subjects Data recorded on an ELSCINT APEX 415 ECT gamma camera, as usually done for cine-oesophagogastroscintigraphy (1 frame/12.5 s; 144 frames). Gastric emptying was observed carefully for 5-6 h, serial images being recorded at 1, 2, 3 and 6 h. Overlapping loops of jejunum and stomach were identified by onward propulsion of the isotope in the bowel. ECT recording (180°, 64×64 matrix) was performed 1 h after ingestion of the antacid composition of example 1. A thyroid scanning was carried out to be sure that no radioactivity had accumulated in the thyroid organ due to the possible presence of free $^{99m}$Tc. A perchlorate test was carried out 5.5 h after the ingestion of the labelled example 1 antacid composition, in order to verify that no free pertechnetate remained on the gastric mucous membrane (the perchlorate compound displaces the pertechnetate product when it has been taken up by the gastric mucous membrane). The results of the isotope scans were considered independently from clinical histories and endoscopic findings.

4) Gastric radioactivity:

Recorded radioactivies in the gastric area drawn on the screen were obtained as a function of time.

5) Results:

The results thus obtained are given hereinafter in table V for the 10 patients with normal gastric mucous membrane (as proven fibroscopically) and for the 14 patients with a proven gastric or duodenal ulcer.

C. Supplemental Assays

Supplemental assays were carried out on 30 voluntary subjects having no gastric ulceration, taken as a control batch, and on 20 voluntary patients suffering from gastric or duodenal ulceration, taken as a treated batch. Each subject and patient received per oral route 22 g of aluminum phosphate gel labelled with $^{99m}$Tc-HMDP. A time-activity curve was drawn using the average activities for the two groups at t=0 h, t=0.5 h, t=1 h, t=2 h and t=3 h.

Taking into account the results as obtained an exponential mathematical model, which can be of the bi-exponential or multi-exponential type, was tested to illustrate both the adhesiveness and anti-adhesiveness of the Al-containing material (here an aluminum phosphate gel) in the stomach.

The best exponential mathematical model regarding the gastric emptying curve is here a bi-exponential one comprising two compartments, namely $$y = \underbrace{A_1 e^{-\frac{0.693t}{T1}}}_{\text{"1"}} + \underbrace{A_2 e^{-\frac{0.693t}{T2}}}_{\text{"2"}}$$

wherein y is the percentage of ingested aluminum phosphate gel in the stomach as a function of the time (t);

t is the time duration, expressed in minutes from the beginning of the measure;

compartment 1 represents the $^{99m}$Tc-HMDP-labelled AlPO$_4$ gel which is free in the stomach;

compartment 2 represents the AlPO$_4$ gel labelled with $^{99m}$Tc-HMDP which adheres to the gastric mucous membrane;

$T_1$ is the time (expressed in minutes) of half evacuation of the free AlPO$_4$-containing material present in the stomach [$T_1$ is also called the "half-time" of compartment 1];

$T_2$ is the time (expressed in minutes) of half evacuation of the bound AlPO$_4$-containing material adhering in the stomach on the mucous gastric membrane [$T_2$ is also called the "half-time" of compartment 2];

$A_1$ is the percentage of AlPO$_4$-containing material in compartment 1 at t=0;

$A_2$ is the percentage of AlPO$_4$-containing material in compartment 2 at t=0.

According to the results thus obtained:

$T_1$ is comprised between 8 and 15 min
$T_2$ is comprised between 30 and 90 min
$A_1$ is comprised between 25 and 45%
$A_2$ is comprised between 75 and 55%.

To be precise, the best bi-exponential curve model, which was obtained in those experiments, is the following one $$y = \underbrace{35.96 \, e^{-\frac{0.693t}{12.1}}}_{\text{"1"}} + \underbrace{64.04 \, e^{-\frac{0.693t}{55.6}}}_{\text{"2"}}$$

in which, half-time $T_1$ is 12.1 min, half-time $T_2$ is 55.6 min, $A_1$ is 35.96% and $A_2$ is 64.04%.

In other words, compartment 1 corresponds to the percentage amount of aluminum phosphate gel present in the gastric lumen and not bound to the gastric mucous membrane, while compartment 2 corresponds to the percentage amount of aluminum phosphate gel adhering to the gastric mucous membrane.

In patients with gastric ulceration, the aluminum phosphate gel component of example 1 according to this invention remains bound to ulcer sites for more than 6 h, and in particular for at least 24 h, after ingestion, even after an intervening normal meal. In patients with no gastric ulceration, said aluminum phosphate gel component of example 1 remains bound to the gastric mucous membrane for up to 6 h. Consequently, the Al-containing material, i.e. here the aluminum phosphate gel, exhibits a specific site-protecting effect on the gastric mucous membrane.

From a theoretical point of view (which does not bind the Applicants), it is strongly believed that both the Al-adhesiveness (or anti-ulceration) and antacid properties are dependent upon an ionic excess of Al$^{+3}$ with respect to Mg$^{+2}$, as illustrated by the weight ratio R comprised between from 5.1:1 to 7.0:1, preferably between from 5.5:1 to 6.5:1, and more preferably between from 5.9:1 to 6.1:1.

Moreover the data of the above experiments point out that the composition according to this invention (i) does exhibit, at least, the advantages of the sucralfate compound with respect to the Al-adhesiveness or anti-ulceration property, and (ii) does not exhibit the drawbacks of said sucralfate compound with respect to the antacid property. In short, this invention provides a composition, useful in the treatment of dyspepsia, and which is (a) at least as effective as sucralfate, as an anti-ulceration means, and (b) effective, as an antacid means, unlike sucralfate.

TABLE Ia

ANTACID ACTIVITY
(with an emptying rate of 1.5 ml/min)

| Products | (1) (a) | (1) (b) | (2) (a) | (2) (b) |
|---|---|---|---|---|
| Ex 1 | 300 | 100 | 395 | 128 |
| Ex 2 | 280 | 94 | 380 | 124 |
| Ex 3 | 220 | 76 | 250 | 85 |
| Ex 4 | 218 | 65.4 | 245 | 83.5 |
| CP 1 | 160 | 58 | 180 | 64 |
| CP 2 | 170 | 61 | 175 | 62.5 |
| CP 3 | 180 | 54 | 172 | 61.6 |
| CP 4 | 150 | 55 | 170 | 61 |
| A | 102 | 40.6 | 130 | 49 |
| B | 200 | 70 | 180 | 64 |
| C | 160 | 58 | 160 | 58 |

Notes
(1) "gastric" reservoir loaded with 100 ml of 0.1 N HCl (pH 1.0)
(2) "gastric" reservoir loaded with 100 ml of 0.1 N HCl and equipped with a gastric mucous membrane
(a) time (min) to return to pH 1.0
(b) mmol $H^+$ neutralized

TABLE Ib

ANTACID ACTIVITY
(with an emptying rate of 3.0 ml/min)

| Products | (1) (a) | (1) (b) | (2) (a) | (2) (b) |
|---|---|---|---|---|
| Ex 1 | 135 | 50.5 | 180 | 64 |
| Ex 2 | 130 | 49 | 172 | 61.6 |
| Ex 3 | 110 | 43 | 125 | 47.5 |
| Ex 4 | 108 | 42.4 | 121 | 46.5 |
| CP 1 | 81 | 34.3 | 90 | 37 |
| CP 2 | 80 | 34 | 89 | 36.7 |
| CP 3 | 75 | 32.5 | 80 | 34 |
| CP 4 | 70 | 31 | 78 | 33.4 |
| A | 75 | 32.5 | 95 | 38.5 |
| B | 80 | 34 | 95 | 38.5 |
| C | 65 | 29.5 | 70 | 31 |

Notes
(1) "gastric" reservoir loaded with 100 ml of 0.1 N HCl (pH 1.0)
(2) "gastric" reservoir loaded with 100 ml of 0.1 N HCl and equipped with a gastric mucous membrane
(a) time (min) to return to pH 1.0
(b) mmol $H^+$ neutralized

TABLE Ic

ANTACID ACTIVITY
(with an emptying rate of 4.5 ml/min)

| Products | (1) (a) | (1) (b) | (2) (a) | (2) (b) |
|---|---|---|---|---|
| Ex 1 | 65 | 29.5 | 95 | 38.5 |
| Ex 2 | 62 | 28.6 | 90 | 37 |
| Ex 3 | 59 | 27.7 | 79 | 33.7 |
| Ex 4 | 58 | 27.4 | 73 | 31.9 |
| CP 1 | 55 | 26.5 | 59 | 27.7 |
| CP 2 | 55 | 26.5 | 59 | 27.7 |
| CP 3 | 51 | 25.3 | 52 | 26.6 |
| CP 4 | 50 | 25 | 52 | 26.6 |
| A | 55 | 26.5 | 70 | 31 |
| B | 55 | 26.5 | 60 | 28 |
| C | 48 | 24.4 | 50 | 25 |

Notes
(1) "gastric" reservoir loaded with 100 ml of 0.1 N HCl (pH 1.0)
(2) "gastric" reservoir loaded with 100 ml of 0.1 N HCl and equipped with a gastric mucous membrane
(a) time (min) to return to pH 1.0
(b) mmol $H^+$ neutralized

TABLE II

ANTACID ISOLATING CAPACITY
(pH measured at 1-15 minutes)

| Products | 1 | 2 | 3 | 4 | 5 | 6 | 7 | 8 |
|---|---|---|---|---|---|---|---|---|
| Ex 1 (a) | 5.86 | 4.91 | 4.0 | 3.37 | 3.0 | 2.78 | 2.62 | 2.49 |
| Ex 2 (b) | 5.75 | 4.80 | 3.8 | 3.09 | 2.8 | 2.69 | 2.60 | 2.48 |
| Ex 3 (c) | 5.25 | 4.62 | 3.51 | 3.08 | 2.7 | 2.65 | 2.58 | 2.47 |
| Ex 4 (d) | 5.20 | 4.59 | 3.49 | 3.02 | 2.68 | 2.63 | 2.57 | 2.46 |
| CP 1 (e) | 3.0 | 2.56 | 2.05 | 1.68 | 1.28 | 1.12 | 1.10 | 1.08 |
| CP 2 (f) | 2.90 | 2.70 | 2.10 | 1.69 | 1.27 | 1.10 | 1.08 | 1.07 |
| CP 3 (g) | 2.89 | 2.68 | 2.06 | 1.65 | 1.27 | 1.09 | 1.06 | 1.05 |
| CP 4 (h) | 3.08 | 2.79 | 2.05 | 1.64 | 1.28 | 1.15 | 1.11 | 1.09 |
| A (i) | 1.77 | 1.01 | 1.00 | 1.00 | 1.00 | — | — | — |
| B (j) | 1.75 | 1.01 | 1.00 | 1.00 | 1.00 | — | — | — |
| C (k) | 3.0 | 2.77 | 2.18 | 1.71 | 1.38 | 1.20 | 1.12 | 1.09 |
| D (l) | 1.74 | 1.01 | 1.00 | 1.00 | 1.00 | — | — | — |
| E (m) | 1.16 | 1.03 | 1.01 | 1.02 | 1.00 | 1.00 | 1.00 | — |

| Products | 9 | 10 | 11 | 12 | 13 | 14 | 15 |
|---|---|---|---|---|---|---|---|
| Ex 1 (a) | 2.39 | 2.39 | 2.20 | 2.10 | 2.0 | 1.9 | 1.79 |
| Ex 2 (b) | 2.38 | 2.37 | 2.10 | 2.0 | 1.9 | 1.75 | 1.62 |
| Ex 3 (c) | 2.37 | 2.36 | 2.10 | 2.0 | 1.9 | 1.75 | 1.62 |
| Ex 4 (d) | 2.37 | 2.36 | 2.09 | 1.99 | 1.88 | 1.74 | 1.61 |
| CP 1 (e) | 1.05 | 1.03 | 1.02 | 1.02 | 1.02 | 1.01 | 1.01 |
| CP 2 (f) | 1.04 | 1.03 | 1.02 | 1.01 | 1.01 | 1.01 | 1.01 |
| CP 3 (g) | 1.03 | 1.02 | 1.01 | 1.01 | 1.01 | 1.01 | 1.01 |
| CP 4 (h) | 1.06 | 1.05 | 1.04 | 1.03 | 1.02 | 1.02 | 1.02 |
| A (i) | — | — | — | — | — | — | — |
| B (j) | — | — | — | — | — | — | — |
| C (k) | 1.07 | 1.05 | 1.04 | 1.03 | 1.03 | 1.02 | 1.02 |
| D (l) | — | — | — | — | — | — | — |
| E (m) | — | — | — | — | — | — | — |

Notes
weight of coating
(a): 0.2443 g;
(b): 0.2451 g;
(c): 0.2463 g;
(d): 0.2440 g;
(e): 0.2438 g;
(f): 0.2425 g;
(g): 0.2428 g;
(h): 0.2430 g;
(i): 0.2377 g;
(j): 0.2381 g;
(k): 0.3117 g;
(l): 0.2576 g; and
(m): 0.181 g.

TABLE III

RADIOPHARMACEUTICAL STABILITY IN VITRO
($AlPO_4$ gel bound activity after 2 h with HCl or NaCl)

| | HCl (20/10 °Be) | | HCl (20/21 °Be 50% diluted) | | NaCl (9 g/l) | |
|---|---|---|---|---|---|---|
| | (1) | (2) | (1) | (2) | (1) | (2) |
| 1 | | 83 | | 12 | | 68 | 19 | 92 |
| 2 | | 72 | | 13 | | 67 | 20 | 96 |
| 3 | | 71 | | 14 | | 72 | 21 | 100 |
| 4 | | 77 | | 15 | | 79 | 22 | 97 |
| 5 | | 73 | | 16 | | 81 | | |
| 6 | | 67 | | 17 | | 69 | | |
| 7 | | 73 | | 18 | | 73 | | |
| 8 | | 74 | | | | | | |
| 9 | | 75 | | | | | | |
| 10 | 76 | | | | | |
| 11 | 77 | | | | | |
| Mean: | 74 | | Mean: | 73 | Mean: | 96 |
| SD: | ±4.08 | | SD: | ±5.44 | SD: | ±3.3 |

Notes
(1) sample No
(2) % bound

TABLE IV

STABILITY IN VITRO OF $AlPO_4$ GEL BOUND ACTIVITY
(in digestive juice after 2 h)

| Sample No | pH of digestive juice pH (source) | $AlPO_4$ gel bound activity (% of bound activity) |
|---|---|---|
| 1 | 1.7 (gastric juice) | 92 |
| 2 | 6.03 (duodenal juice) | 93 |
| 3 | 6.57 (duodenal juice) | 87 |

TABLE IV-continued

STABILITY IN VITRO OF AlPO$_4$ GEL BOUND ACTIVITY
(in digestive juice after 2 h)

| Sample No | pH of digestive juice pH (source) | | AlPO$_4$ gel bound activity (% of bound activity) |
|---|---|---|---|
| 4 | 2.16 | (gastric juice) | 89 |
| 5 | 6.8 | (duodenal juice) | 96 |
| | | Mean: | 91 |
| | | SD: | ±4 |

TABLE V

| Patients with | Endoscopic examination | Positive scan AlPO$_4$ labelled with $^{99m}$Tc-HMDP |
|---|---|---|
| gastric ulcers | 11 | 11 |
| duodenal ulcers | 3 | 3 |
| normal gastro-intestinal membrane | 10 | 0 |

What is claimed is:

1. An antacid composition comprising, in association with a physiologically acceptable excipient, a pharmaceutically effective amount of a mixture of
    (a) an Al-containing material, aluminum phosphate gel, which normally adheres to the gastrointestinal mucous membrane, as a first pharmaceutically active component, and
    (b) a Mg-containing material selected from a group consisting of MgO, Mg(OH)$_2$ and mixtures thereof, which normally does not adhere to the gastrointestinal mucous membrane, as a second pharmaceutically active components,
    wherein the weight ratio of Al in said Al-containing material to Mg in said Mg-containing material is between from 5.1:1 to 7.0:1.

2. An antacid composition according to claim 1, wherein said AlPO$_4$-containing material is an aluminum phosphate gel which contains from 5 to 45% by weight of AlPO$_4$.

3. An antacid composition according to claim 1, wherein said AlPO$_4$-containing material is an aluminum phosphate gel which contains 20% by weight of AlPO$_4$.

4. An antacid composition according to claim 3, wherein MgO is the second component.

5. An antacid composition according to claim 1, wherein said weight ratio R=Al/Mg is comprised between from 5.5:1 to 6.5:1.

6. An antacid composition according to claim 1, wherein said weight ratio R=Al/Mg is comprised between from 5.9:1 to 6.1:1.

7. A method of treatment of dyspepsia induced by gastric hyperacidity which comprises administering to a human being in need of said treatment a therapeutically effective amount of an antacid composition; said antacid composition comprising in association with a physiologically acceptable excipient, a pharmaceutically effective amount of a mixture of
    (a) Al-containing material, aluminum phosphate gel, which normally adheres to the gastrointestinal mucous membrane, as a first pharmaceutically active component, and
    (b) a Mg-containing material selected from a group consisting of MgO, Mg(OH)$_2$ and mixtures thereof, which normally does not adhere to the gastrointestinal mucous membrane, as a second pharmaceutically active component.
    wherein the weight ratio of Al in said Al-containing material to Mg in said Mg-containing material is between from 5.1:1 to 7.0:1.

8. A method of treatment according to claim 7, wherein said composition has a weight ratio R=Al/Mg comprised between from 5.5:1 to 6.5:1.

9. A method of treatment according to claim 7, wherein said composition has a weight ratio R=Al/Mg comprised between from 5.9:1 to 6.1:1.

10. A method of treatment according to claim 7, wherein said composition contains per unit dosage (a) 9.904 g of aluminum phosphate gel comprising 20% by weight of AlPO$_4$ and (b) 0.122 g of MgO.

11. A method of treatment of dyspepsia induced by gastric hyperacidity which comprises administering to a human being in need of said treatment a therapeutically effective amount of an antacid composition; said antacid composition comprising in association with a physiologically acceptable excipient, pharmaceutically effective amount of a mixture of
    (a) Al-containing material, aluminum phosphate gel, which normally adheres to the gastrointestinal mucous membrane for a time providing an Al-adhesiveness duration, as a first pharmaceutically active component, and
    (b) a Mg-containing material selected from a group consisting of MgO, Mg(OH)$_2$ and mixtures thereof, which normally does not adhere to the gastrointestinal mucous membrane, as a second pharmaceutically active component,
    wherein the weight ratio of Al in said Al-containing material to Mg in said Mg-containing material is between from 5.1:1 to 7.1:1, wherein the Al-adhesiveness duration on the gastrointestinal mucous membrane is for more than six hours or at least 24 hours after ingestion on the ulceration sites of said gastrointestinal mucous membrane.

* * * * *